US000001340H

United States Statutory Invention Registration [19]

[11] Reg. Number: H1340

[43] Published: Jul. 5, 1994

Yetter et al.

[54] DISPOSABLE SANITARY GARMENT

[76] Inventors: Jerry J. Yetter; Charles D. Broaddus, both of The Procter & Gamble Company, Miami Valley Laboratories, P.O. Box 398707, Cincinnati, Ohio 45239-8707

[21] Appl. No.: 855,148

[22] Filed: Mar. 20, 1992

Related U.S. Application Data

[63] Continuation of Ser. No. 758,253, Aug. 26, 1991, abandoned, which is a continuation of Ser. No. 452,998, Dec. 19, 1989, abandoned.

[51] Int. Cl.[5] ..... A61F 13/16

[52] U.S. Cl. ..... 604/376; 604/364; 604/368

[58] Field of Search ..... 604/358, 364, 374, 375, 604/376, 367, 368, 891.1; 602/41, 48; 606/77, 230, 231, 213

[56] References Cited

U.S. PATENT DOCUMENTS

| | | | |
|---|---|---|---|
| 781,142 | 1/1905 | Manrath | 128/155 |
| 835,083 | 11/1906 | Strahl | 128/155 |
| 2,404,758 | 7/1946 | Teague et al. | 128/155 |
| 3,595,235 | 7/1971 | Jespersen | 604/364 |
| 3,896,802 | 7/1975 | Williams | 128/156 |
| 4,337,181 | 6/1982 | Otey et al. | 523/128 |
| 4,372,311 | 2/1983 | Potts | 604/364 |
| 4,685,909 | 8/1987 | Berg et al. | 604/375 |
| 4,923,454 | 5/1990 | Seymour et al. | 604/368 |
| 4,944,734 | 7/1990 | Wallach | 604/358 |
| 5,180,765 | 1/1993 | Sinclair | 524/306 |

OTHER PUBLICATIONS

Remington's Pharmaceutical Sciences 15th Edition (1975) p. 1778, Mack Publishing Company, Easton, Pa., Ibid. p. 1775.

New Scientist, Nov. 25, 1989, p. 37.

*Primary Examiner*—David Brown

[57] ABSTRACT

Disposable sanitary garments comprise topsheet and/or backsheet materials prepared from polymers based on glycolic acid, lactic acid, and mixtures thereof. Disposable sanitary articles having absorbent cores comprising oxidized cellulose are also provided. Diapers, sanitary napkins, pantiliners, and the like, prepared from the foregoing materials are disclosed.

15 Claims, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

DISPOSABLE SANITARY GARMENT

This is a continuation of application Ser. No. 07/758,253, filed on Aug. 26, 1991, now abandoned, which is a continuation of application Ser. No. 07/452,998, filed on Dec. 19, 1989, now abandoned.

Technical Field

The present invention relates to disposable absorbent articles such as diapers, sanitary napkins, pantiliners, and the like, which are especially adapted for absorbing various bodily fluids. The articles herein are prepared from topsheet and/or backsheet and/or absorbent core materials which are designed to enhance their disposability.

BACKGROUND OF THE INVENTION

A wide variety of absorbent structures designed to be efficient for the absorption of body fluids such as blood, urine, menses, and the like, are known. Disposable products of this type generally comprise some sort of fluid-permeable topsheet material, an absorbent core, and a fluid-impermeable backsheet material.

Heretofore, such absorbent structures have been prepared using, for example, topsheet materials prepared from woven, nonwoven, or porous formed-film polyethylene or polypropylene materials. Backsheet materials typically comprise flexible polyethylene sheets. Absorbent core materials typically comprise wood pulp fibers or wood pulp fibers in combination with absorbent gelling materials.

One aspect of such sanitary products which has recently been considered is their disposability. Although such products largely comprise materials which would be expected ultimately to degrade, and although products of this type contribute only a very small percentage of the total solid waste materials generated by consumers each year, nevertheless, there is currently a perceived need to devise such disposable products from materials which degrade relatively quickly, thereby lessening their bulk.

The practice of the present invention draws upon the well-known teachings of the surgical arts to meet the aforesaid disposability issue. In particular, those aspects of the surgical arts relating to sutures and hemostats are employed in the practice of this invention to provide desirable topsheet, backsheet and absorbent core materials.

More particularly, the present invention employs the types of materials used by surgeons in synthetic absorbable sutures to provide topsheet and backsheet materials which can be used to fashion diapers, sanitary napkins, pantiliners, and the like. Such suture materials, especially those based on glycolic acid and/or lactic acid, as described hereinafter, are designed to degrade by simple hydrolysis, e.g., in landfills. The oxidized celluloses employed as absorbent cores herein are also well-known from surgical arts as absorbent hemostatic materials. Such materials are also broken down by natural biological processes, thereby enhancing their disposability.

In short, the present invention uses conventional knowledge from the medical arts relating to absorbable, hydrolyzable and biodegradable surgical materials, and reapplies such materials in an unconventional way to prepare disposable sanitary products for use by the consumer.

BACKGROUND ART

The present invention relates to the preparation of diapers, sanitary napkins, pantiliners, and the like, all of which have been described in great detail in patents and other literature. A wide variety of such articles are commercially available. It is to be understood that this invention does not relate to the manufacture of any particular type, shape or style of such articles; rather, the invention herein relates to the particular choice of topsheet, backsheet and core materials which can be used in the manufacture of such articles to make them more disposable.

The preparation of surgical sutures from degradable polymers is described in REMINGTON'S PHARMACEUTICAL SCIENCES 15th Edition (1975) p. 1778, Mack Publishing Company, Easton, Pa.

The preparation of oxidized cellulose for use as absorbable surgical hemostats is described ibid., p. 1775.

The journal NEW SCIENTIST, Nov. 25, 1989, p. 37, mentions the use of polymers made from lactic acid as being useful as biodegradable plastics. The use of such polymers in dissolving sutures and bags is mentioned.

SUMMARY OF THE INVENTION

The present invention encompasses disposable absorbent structures, comprising a water-permeable topsheet, an absorbent core, and a water-impermeable backsheet, said structures being characterized in that said backsheet comprises a flexible film comprising a lactic acid-based or glycolic acid-based polyester. Said polyester backsheet can also comprise a co-polyester based on glycolic acid and lactic acid.

The invention also encompasses disposable absorbent structures, comprising said water-permeable topsheet, absorbent core and water-impermeable backsheet, said structures being characterized in that said topsheet comprises a flexible porous sheet or woven or nonwoven web of polymer comprising a lactic acid-based or glycolic acid-based polyester. Again, the polyester topsheet can also comprise a co-polyester based on lactic acid and glycolic acid. Such topsheets are preferably in the form of a nonwoven web.

In another aspect, the invention encompasses disposable absorbent structures comprising a water-permeable topsheet, a water-impermeable backsheet, and an absorbent core, said structures being characterized in that said absorbent core comprises oxidized cellulose. Typically, the oxidized cellulose comprises at least 16% carboxyl groups.

Other structures according to this invention are those wherein both the topsheet and the backsheet comprise a lactic acid-based or glycolic acid-based polyester, or co-polyester thereof. Still other structures have both topsheet and backsheet prepared from the foregoing polyesters, and also have oxidized cellulose comprising the absorbent core. The oxidized cellulose absorbent core can also contain an absorbent gelling material to provide additional absorbent capacity.

Structures according to any of the foregoing embodiments of the invention are provided in the form of disposable diapers, sanitary napkins or pantiliners.

All ratios, proportions and percentages herein are by weight, unless otherwise specified.

DETAILED DESCRIPTION

The polyesters employed to prepare the topsheet and backsheet materials employed herein are based on glycolic acid ($HOCH_2COOH$), lactic acid ($CH_3CHOHCOOH$) and mixtures thereof. Glycolic acid is available commercially from the oxidation of ethylene glycol with dilute acid; by the hydrolysis of chloroacetic acid; or by the reaction of formaldehyde with carbon monoxide. Lactic acid is available from various fermentation processes, using any convenient lactose source. As is known from the literature, these acids can be reacted using well-known reaction conditions to form polyester polymers. In a typical reaction, the cyclic derivative of glycolic acid (glycolide) and/or the cyclic derivative of lactic acid (lactide), or mixtures thereof (i.e., to form "co-polyesters"), are polymerized. Typically, molecular weights range from several hundred thousand to several million.

Figure 1:
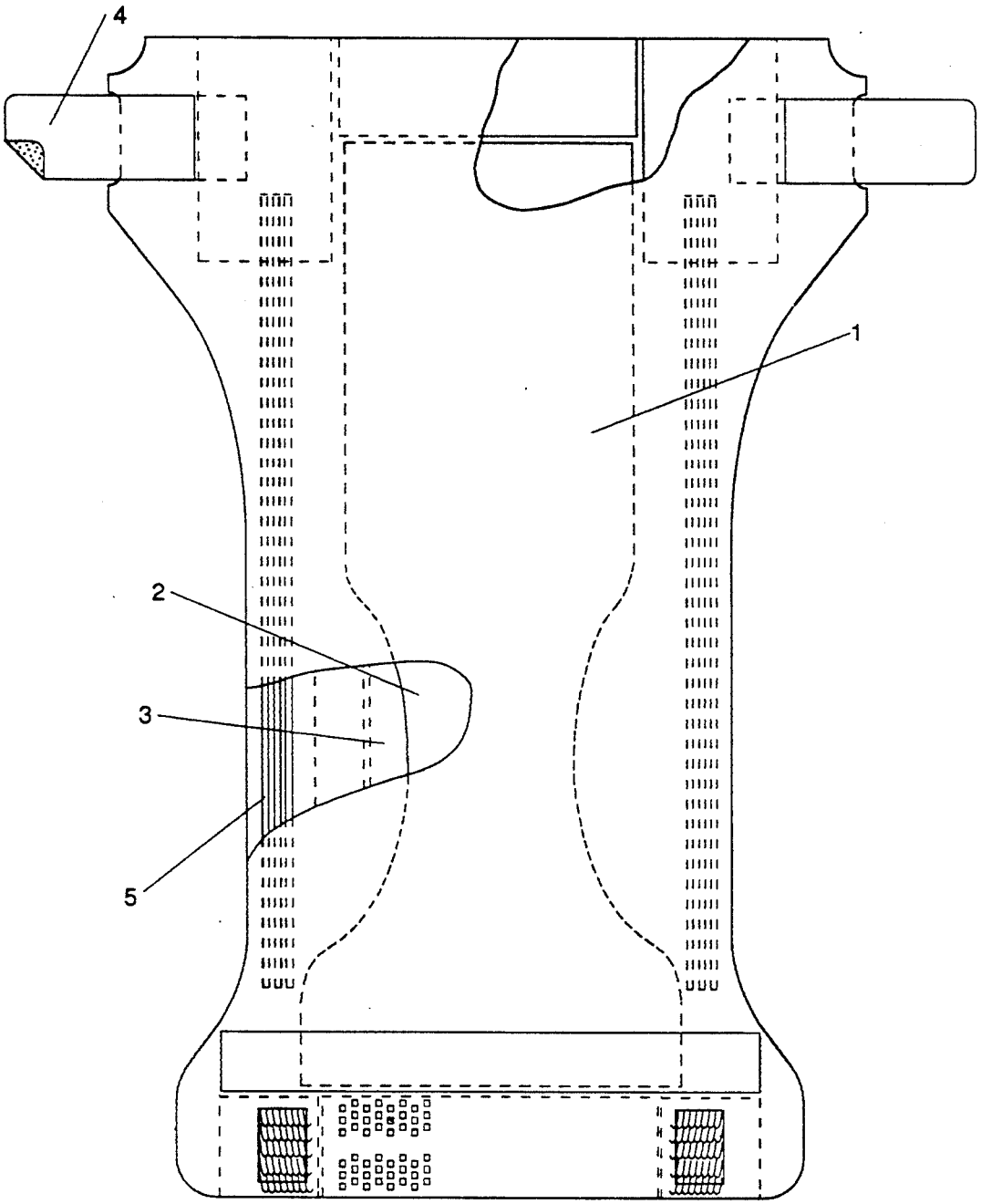
FIG. 1 is a plan view, partially cut away to reveal internal structure of a disposable diaper.

The apparatus shown in FIG. 1 illustrates a typical disposable diaper of the type found in commerce in which the disposable absorbent materials would be employed. FIG. 1 is comprised of a topsheet (1) superposed over an absorbent core (2), which, in turn, is superposed over a backsheet (3). Optional tape fasteners (4) and leg band elastics (5), both of which are conventional on modern disposable diapers, are also shown.

Figure 2:
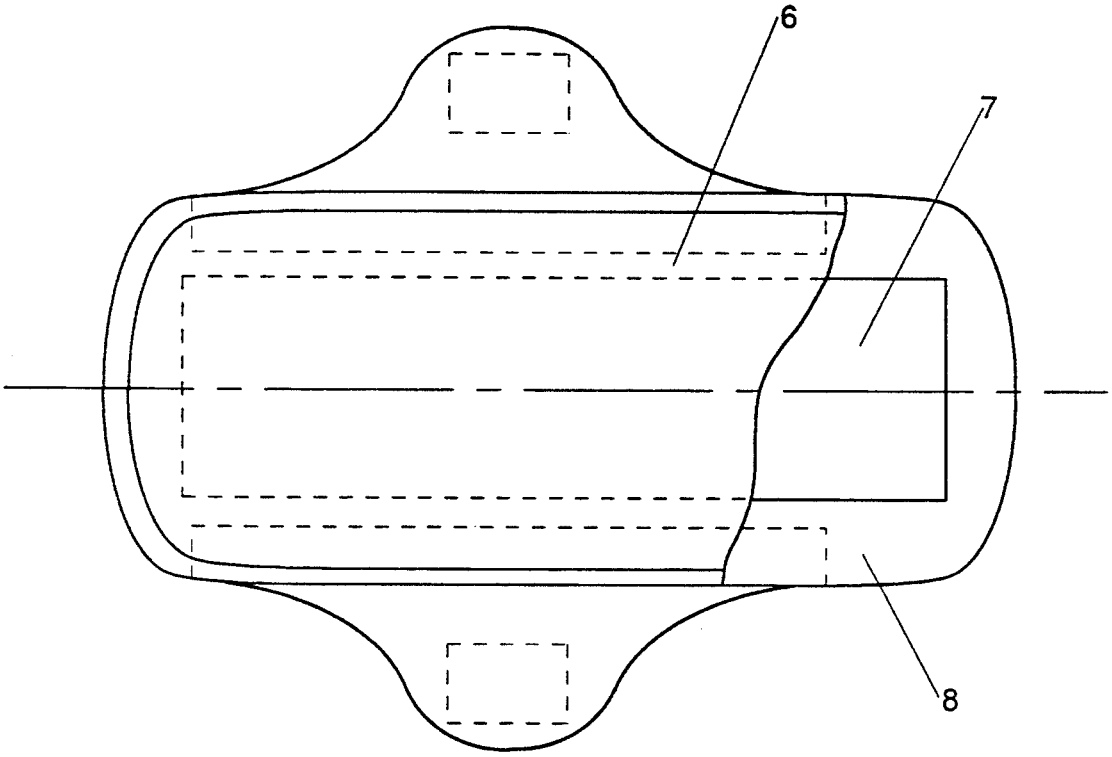
FIG. 2 is a plan view, partially cut away to reveal internal structure of a sanitary napkin or panti-liner.

Additionally, the apparatus shown in FIG. 2 illustrates a typical sanitary napkin or panti-liner of the type typically found in commerce in which the disposable absorbent materials would be employed. FIG. 2 is comprised of a topsheet (6), absorbent core (7), and backsheet (8).

For use as topsheet materials, the foregoing glycolic acid-based or lactic acid-based polyesters can be cast as sheets having a multiplicity of perforations therethrough, or can be used in the form of filaments to prepare a woven or nonwoven web. The formation of perforated sheets and webs for use as topsheets is well-known in the art. The same manufacturing principles apply when such sheet or webs are made using the polyesters herein. For use as backsheet materials, the aforesaid polyesters are simply cast into nonperforate, flexible sheets (typically 0.01 mm to 2 mm thickness).

It is to be understood that the articles herein can comprise either the topsheet, the backsheet, or both, made from the aforementioned polyester polymers.

The oxidized cellulose absorbent material can be prepared by the mild oxidation of any convenient source of cellulose, e.g., wood pulp, cotton, and the like. Oxidized cotton is available from Parke-Davis in the form of gauze, strips and pads. Typically, the oxidized cellulose contains at least 16% (generally 16–24%) carboxyl groups.

It is to be understood that the articles herein can be prepared using either oxidized cellulose or ordinary cellulose fibers as the absorbent core. Moreover, said cores can also contain additional absorbent materials, especially the high fluid capacity absorbent gelling materials commonly used in modern diapers and sanitary napkins. Such materials include, for example, acrylates, starch grafted alkylates, and various gums and/or saccharidic gelling materials which absorb and hold 10–50 times their weight of water. Such materials are thoroughly described in the voluminous patent literature relating to disposable sanitary products, and are available from various commercial sources.

The following Examples illustrate the practice of this invention.

EXAMPLE I

A disposable baby diaper according to this invention is prepared as follows. The dimensions listed are for a diaper intended for use with a child in the 6–10 kilogram size range. These dimensions can be modified proportionately for different size children, or for adult incontinence briefs, according to standard practice.

1. Backsheet: 0.025–0.070 mm polyglycolate film; width at top and bottom 33 cm; notched inwardly on both sides to a width-at-center of 28.5 cm; length 50.2 cm.
2. Topsheet: nonwoven fabric scrim comprising lactate/glycolate co-polyester fibers; width at top and bottom 33 cm; notched inwardly on both sides to a width-at-center of 28.5 cm; length 50.2 cm.
3. Absorbent core: oxidized cellulose (16–24% carboxyl); 8.4 mm thick, calendered; width at top and bottom 28.6 cm; notched inwardly at both sides to a width-at-center of 10.2 cm; length 44.5 cm.
4. Elastic leg bands: four individual rubber strips (2 per side); width 4.77 mm; length 370 mm; thickness 0.178 mm (all the foregoing dimensions being in the relaxed state).

The diaper of Example I is prepared in standard fashion by positioning the core material covered with the topsheet on the backsheet and gluing.

The elastic bands (designated "inner" and "outer", corresponding to the bands closest to, and farthest from, the core, respectively) are stretched to ca. 50.2 cm and positioned between the topsheet/backsheet along each longitudinal side (2 bands per side) of the core. The inner bands along each side are positioned ca. 55 mm from the narrowest width of the core (measured from the inner edge of the elastic band). This provides a spacing element along each side of the diaper comprising the flexible topsheet/backsheet material between the inner elastic and the curved edge of the core. The inner bands are glued down along their length in the stretched state. The outer bands are positioned ca. 13 mm from the inner bands, and are glued down along their length in the stretched state. The topsheet/backsheet assembly is flexible, and the glued-down bands contract to elasticize the sides of the diaper.

EXAMPLE II

A lightweight pantiliner suitable for use between menstrual periods comprises a pad (surface area 117 $cm^2$; SSK air felt 3.0 g) containing 1.0 g of absorbent gelling material particles (commercial polyacrylate; Nippon Shokubai); said pad being interposed between a porous formed-film topsheet according to U.S. Pat. No. 4,463,045 and a backsheet which comprises a 0.03 mm thickness polyglycolate film.

EXAMPLE III

A catamenial product in the form of a sanitary napkin having two flaps extending outward from its absorbent core is prepared using a pad in the manner of Example II (surface area 117 $cm^2$; 8.5 g SSK air felt), per the design of U.S. Pat. No. 4,687,478, Van Tillburg, Aug. 18, 1987. The backsheet comprises 0.025 mm polyethylene, and the topsheet comprises a nonwoven scrim of polylactate fibers.

EXAMPLE IV

The sanitary napkin of Example III is modified by replacing the topsheet with a porous nonglossy formed film, per U.S. Pat. No. 4,687,478, said film being prepared from a lactate/glycolate co-polyester.

It will be appreciated that the polyester materials herein can, if desired, be physically modified by means of various plasticizer materials, in well-known fashion. Likewise, various polyols and/or compounds containing carboxyl/hydroxyl moieties can be included in the polymerization mixture to modify the polymer properties, according to the desires of the formulator. So long as the lactic acid-derived and/or glycolic acid-derived portion of the polymer remains at least 35% (mole basis), preferably 50% (mole basis) of the resulting polymer, the desired benefits of this invention can be achieved.

What is claimed is:

1. A disposable absorbent structure, comprising a water-permeable topsheet, an absorbent core, and a water-impermeable backsheet, said structure being characterized in that said backsheet comprises a flexible film comprising a lactic acid-based or glycolic acid-based polyester.

2. A structure according to claim 1 wherein the polyester backsheet comprises a co-polyester based on glycolic acid and lactic acid.

3. A structure according to claim 1, in the form of a disposable diaper, sanitary napkin or pantiliner.

4. A structure according to claim 1 wherein both the topsheet and the backsheet comprise a lactic acid-based or glycolic acid-based polyester, or co-polyester thereof.

5. A structure according to claim 4 in the form of a disposable diaper, sanitary napkin or pantiliner.

6. A structure according to claim 4 wherein the absorbent core comprises oxidized cellulose.

7. A structure according to claim 6 in the form of a disposable diaper, sanitary napkin or pantiliner.

8. A disposable absorbent structure, comprising a water-permeable topsheet, an absorbent core and a water-impermeable backsheet, said structure being characterized in that said topsheet comprises a flexible porous sheet or woven or nonwoven web of polymer comprising a lactic acid-based or glycolic acid-based polyester.

9. A structure according to claim 8 wherein the polyester topsheet comprises a co-polyester based on lactic acid and glycolic acid.

10. A structure according to claim 8 wherein the topsheet is in the form of a nonwoven web.

11. A structure according to claim 8 in the form of a disposable diaper, sanitary napkin or pantiliner.

12. A disposable absorbent structure comprising a water-permeable topsheet, a water-impermeable backsheet, and an absorbent core, said structure being characterized in that said absorbent core comprises oxidized cellulose.

13. A structure according to claim 12 wherein the oxidized cellulose comprises at least 16% carboxyl groups.

14. A structure according to claim 12 in the form of a disposable diaper, sanitary napkin or pantiliner.

15. A structure according to claim 12 wherein the oxidized cellulose absorbent core additionally contains an absorbent gelling material.

* * * * *